United States Patent
Tsuchida

(10) Patent No.: US 9,221,849 B2
(45) Date of Patent: Dec. 29, 2015

(54) SILANE COUPLING AGENT, MAKING METHOD, PRIMER COMPOSITION, AND COATING COMPOSITION

(71) Applicant: Shin-Etsu Chemical Co., Ltd., Tokyo (JP)

(72) Inventor: Kazuhiro Tsuchida, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/584,491

(22) Filed: Dec. 29, 2014

(65) Prior Publication Data

US 2015/0210721 A1    Jul. 30, 2015

(30) Foreign Application Priority Data

Jan. 24, 2014   (JP) .................................. 2014-011405

(51) Int. Cl.
    *C09D 7/12*      (2006.01)
    *C07F 7/18*      (2006.01)

(52) U.S. Cl.
    CPC ............ *C07F 7/1868* (2013.01); *C09D 7/1233* (2013.01)

(58) Field of Classification Search
    CPC ........................... C09D 7/1233; C07F 7/1868
    See application file for complete search history.

(56) References Cited

U.S. PATENT DOCUMENTS 8,338,510 B2    12/2012   Suwa

FOREIGN PATENT DOCUMENTS

| JP | 2009-15285 A | 1/2009 |
| JP | 2010-152302 A | 7/2010 |
| JP | 4817710 B2 | 11/2011 |
| JP | 2011-256394 A | 12/2011 |
| JP | 5034901 B2 | 9/2012 |
| WO | WO 2009/096050 A1 | 8/2009 |
| WO | WO 2011/114995 A1 | 9/2011 |

*Primary Examiner* — Joseph Kosack
(74) *Attorney, Agent, or Firm* — Birch, Stewart, Kolasch & Birch, LLP

(57) ABSTRACT

A silane coupling agent is obtained from high-temperature heat distillation reaction of a silane coupling agent having a customary amic acid structure group. Dealcoholization reaction takes place between the carboxylic acid group and the alkoxysilyl group in the structure to induce intramolecular crosslinking. The crosslinked polymer component exerts a remarkable adhesion promoting effect.

16 Claims, 1 Drawing Sheet

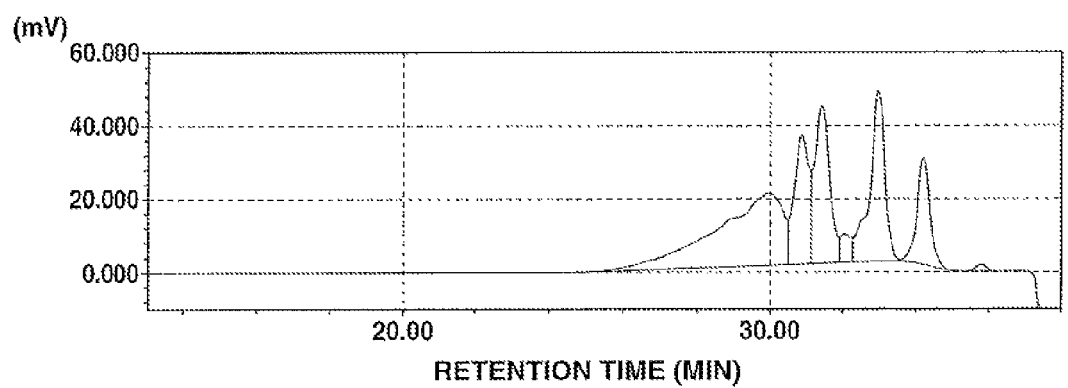

SILANE COUPLING AGENT, MAKING METHOD, PRIMER COMPOSITION, AND COATING COMPOSITION

CROSS-REFERENCE TO RELATED APPLICATION

This non-provisional application claims priority under 35 U.S.C. §119(a) on Patent Application No. 2014-011405 filed in Japan on Jan. 24, 2014, the entire contents of which are hereby incorporated by reference.

TECHNICAL FIELD

This invention relates to a silane coupling agent and a method for preparing the same, and more particularly to a silane coupling agent for use as a primer or adhesion promoter suited for bonding of highly polar, heat resistant resin materials, typically polyimides to metals, and a method for preparing the same. It also relates to a primer composition and a coating composition comprising the silane coupling agent.

BACKGROUND ART

Organosilicon compounds having a hydrolyzable silyl group and an organic reactive group are generally known as "silane coupling agents" and often used as adhesives, paint additives and resin modifiers, for example, since they are capable of forming bonds between inorganic materials and organic materials.

Typical of the organic reactive group are vinyl, amino, epoxy, (meth)acrylic, mercapto, isocyanate, ketimine structure, and styryl groups. Silane coupling agents having such groups are well known and used in a variety of applications.

As the requirements on physical properties become severer in many applications, the organic material or resin used therein makes a transition from general-purpose materials to special materials like super-engineering plastics. The silane coupling agent capable of improving adhesion to such special materials is not necessarily limited to those having the above functional groups. There is a need for a silane coupling agent having a functional group compatible with an individual resin material.

Included in the silane coupling agent suited for use with highly polar, heat-resistant organic materials such as polyimides and polyamides are silane coupling agents having acid anhydride or amic acid structure in monomer constituent units and imide ring-containing silane coupling agents of similar structure. They are used as an adhesion promoter for resist materials as reported in the literature.

Patent Documents 1 to 4 disclose resist materials comprising silane coupling agents having an imide structure group. These proposals rely on the adhesion promoting effect due to the compatibility and interaction of the imide structure. Since the imide structure itself has no chemical bonding ability, there is still left room for improvement in the desired adhesion.

Also Patent Documents 5 to 7 disclose silane coupling agents having an amic acid structure group and resist materials comprising the silanes. All these documents relate to only silane coupling agent monomers obtained from reaction of an acid anhydride ring-containing silane coupling agent with a primary amine compound, but nowhere refer to high molecular weight products obtained by heating the amic acids. The adhesion promoting effect of these techniques is still insufficient.

CITATION LIST

Patent Document 1: JP-A 2009-015285
Patent Document 2: JP-A 2010-152302
Patent Document 3: JP 5034901
Patent Document 4: WO 2009/096050
Patent Document 5: JP 4817710
Patent Document 6: JP-A 2011-256394
Patent Document 7: WO 2011/114995

DISCLOSURE OF INVENTION

An object of the invention is to provide a silane coupling agent having an amic acid structure group, useful for promoting adhesion in bonding a highly polar, heat-resistant organic material such as polyimide or polyamide to a metal material, and a method for preparing the same. Another object of the invention is to provide a primer composition and a coating composition each comprising the silane coupling agent.

The inventor has found that a silane coupling agent consisting of a mixture of organosilicon compounds having the general formula (1), defined below, is effective for promoting the adhesion between a highly polar, heat-resistant organic material such as polyimide or polyamide and a metal material; and that the silane coupling agent is obtained by reacting a silane coupling agent having a succinic anhydride functional group represented by the general formula (2), defined below, with a primary and/or secondary amine compound having the general formula (3), defined below, in an aprotic organic solvent having a boiling point of at least 140° C., and heating the reaction solution at or above the boiling point of the organic solvent for thereby effecting dealcoholization reaction between the carboxylic acid group and the alkoxysilyl group in the starting silane coupling agent structure while distilling off the organic solvent.

In one aspect, the invention provides a silane coupling agent consisting of a mixture of organosilicon compounds having the general formula (1);

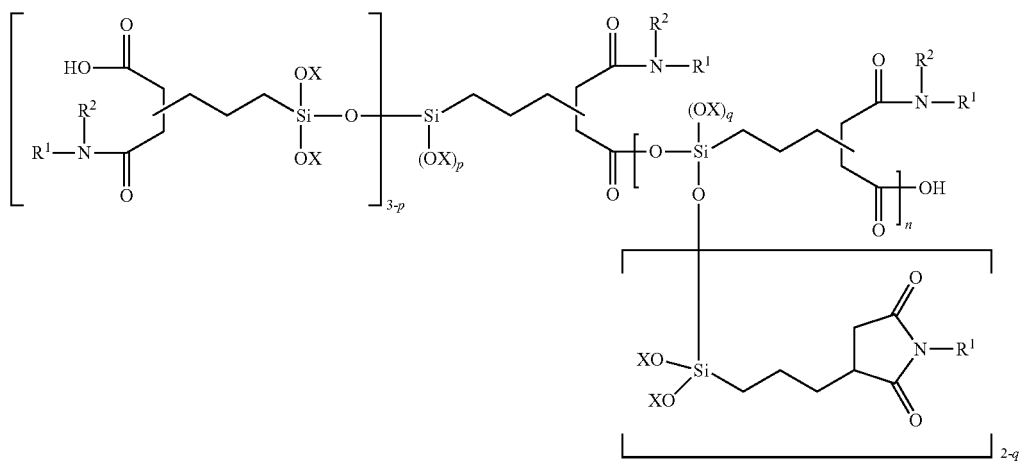

wherein R¹ is independently $C_1$-$C_{10}$ alkyl or $C_1$-$C_{10}$ aryl, $R^2$ is independently hydrogen, $C_1$-$C_{10}$ alkyl or $C_6$-$C_{10}$ aryl, X is independently alkyl or $C_1$-$C_{10}$ aryl, n is an integer of at least 1, p is an integer of 0 to 3, and q is an integer of 0 to 2.

Preferably, $R^2$ is hydrogen, and more preferably $R^1$ is tert-butyl or phenyl.

Preferably, the silane coupling agent has a weight average molecular weight of at least 850 as measured versus polystyrene standards by gel permeation chromatography and contains at least 50% by weight of organosilicon compounds having a weight average molecular weight of at least 600.

In another aspect, the invention provides a method for preparing the silane coupling agent defined above, comprising the steps of reacting a silane coupling agent having a succinic anhydride functional group represented by the general formula (2):

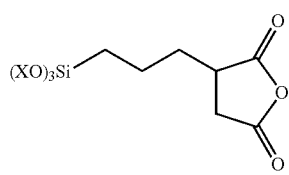

(2)

wherein X is as defined above, with a primary and/or secondary amine compound having the general formula (3)

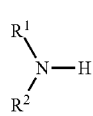

(3)

wherein $R^1$ and $R^2$ are as defined above, in an aprotic organic solvent having a boiling point of at least 140° C., and heating the reaction solution at a temperature equal to or higher than the boiling point of the organic solvent for thereby effecting dealcoholization reaction between the carboxylic acid group and the alkoxysilyl group in the starting silane coupling agent structure while distilling off the organic solvent.

The aprotic organic solvent is preferably propylene glycol monomethyl ether acetate, cyclohexanone or N-methylpyrrolidone.

In a further aspect, the invention provides a primer composition comprising the silane coupling agent defined above.

In a still further aspect, the invention provides a coating composition comprising the silane coupling agent defined above. The coating composition is suitable for use with a photosensitive heat-resistant material.

In a still further aspect, the invention provides an article having a cured film of the coating composition defined above.

Advantageous Effects of Invention

The silane coupling agent having an amic acid structure group is obtained from high-temperature heat distillation reaction of a silane coupling agent having a customary amic acid structure group. Dealcoholization reaction takes place between the carboxylic acid group and the alkoxysilyl group in the structure to induce intramolecular crosslinking. The crosslinked polymer component exerts a remarkable adhesion promoting effect as compared with the monomeric component (i.e., silane coupling agent having a customary amic acid structure group).

BRIEF DESCRIPTION OF DRAWINGS

The only FIGURE, FIG. 1 is a GPC chart of the reaction product obtained in Example 1.

DESCRIPTION OF PREFERRED EMBODIMENTS

As used herein, the notation (Cn-Cm) means a group containing from n to m carbon atoms per group. Mw is a weight average molecular weight as measured by gel permeation chromatography (GPC) versus polystyrene standards.

The silane coupling agent of the invention is represented by the general formula (1).

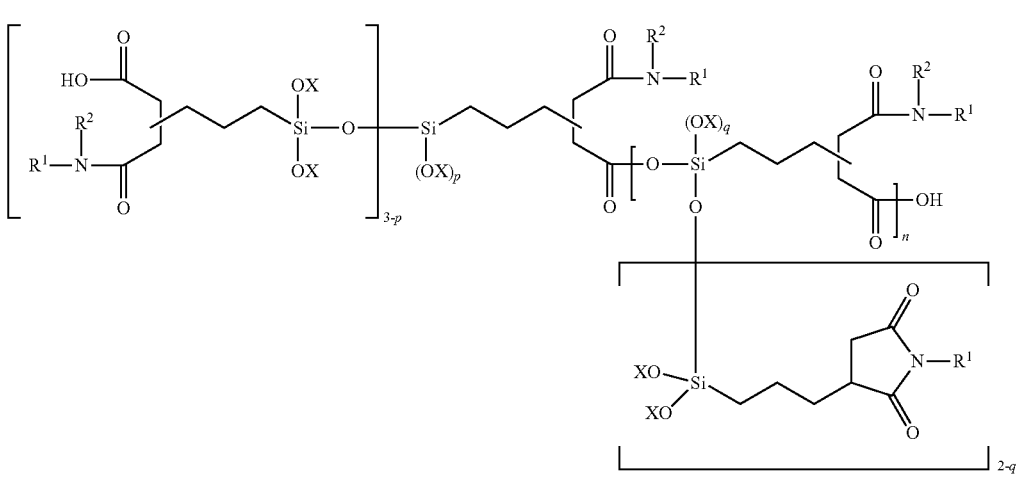

(1)

Herein $R^1$ is independently $C_1$-$C_{10}$ alkyl or $C_6$-$C_{10}$ aryl, $R^2$ is independently hydrogen, $C_1$-$C_{10}$ alkyl or $C_6$-$C_{10}$ aryl, X is independently $C_1$-$C_{10}$ alkyl or $C_1$-$C_{10}$ aryl, n is an integer of at least 1, p is an integer of 0 to 3, and q is an integer of 0 to 2.

More particularly, $R^1$ is independently $C_1$-$C_{10}$ alkyl or $C_6$-$C_{10}$ aryl. Suitable $C_1$-$C_{10}$ alkyl groups include methyl, ethyl, propyl, isopropyl, butyl, isobutyl, tert-butyl, pentyl, hexyl, and cyclohexyl. Suitable $C_6$-$C_{10}$ aryl groups include phenyl and naphthyl. Among others, tert-butyl and phenyl are preferred for availability of the reactant and controlled coloration and heat resistance of the product.

$R^2$ is independently hydrogen, $C_1$-$C_{10}$ alkyl or $C_6$-$C_{10}$ aryl. Suitable $C_1$-$C_{10}$ alkyl groups include methyl, ethyl, propyl, isopropyl, butyl, isobutyl, tert-butyl, pentyl, hexyl, and cyclohexyl. Suitable $C_6$-$C_{10}$ aryl groups include phenyl and naphthyl. Among others, hydrogen is preferred for availability of the reactant and controlled coloration and heat resistance of the product.

As pointed out above, the feature of the invention resides in high-temperature distillation reaction that induces dealcoholization (alcohol elimination) crosslinking between the carboxylic acid group and the alkoxysilyl group and molecular weight buildup. When $R^2$ is hydrogen, imidization can occur in the auric acid structure. In such a case, the reaction forms water as by-product, which is consumed in hydrolytic condensation between alkoxysilyl groups. This results in molecular weight buildup which is also effective for adhesion promotion.

X is independently $C_1$-$C_{10}$ alkyl or $C_6$-$C_{10}$ aryl. Suitable $C_1$-$C_{10}$ alkyl groups include methyl, ethyl, propyl, isopropyl, butyl, isobutyl, tert-butyl, pentyl, hexyl, and cyclohexyl. Suitable $C_6$-$C_{10}$ aryl groups include phenyl and naphthyl. Among others, methyl and ethyl are preferred for availability of the reactant.

The subscript n, indicative of the degree of crosslinking associated with dealcoholization crosslinking reaction between carboxylic acid group and alkoxysilyl group, is an integer of at least 1, preferably at least 2 because satisfactory adhesion is obtainable. If n is less than 1 (n=0), the compound corresponds to simple reaction of a succinic anhydride-containing silane coupling agent with an amine and fails to exert a satisfactory adhesion promoting effect. If n exceeds 20, adhesion promotion is not adversely affected, but such a high molecular weight compound may be less stable in solution form and the productivity may become low when the organic solvent and the distillation time needed in the dealcoholization crosslinking reaction are taken into account. Thus most preferably n is an integer of 2 to 20. The subscript p is an integer of 0 to 3, and q is an integer of 0 to 2.

The silane coupling agent of the invention should preferably have a weight average molecular weight (Mw) of at least 850, more preferably 850 to 6,500, as measured versus polystyrene standards by GPC and contain at least 50% by weight, more preferably 55 to 90% by weight of organosilicon compounds having a Mw of at least 600. Below the ranges, the aforementioned crosslinking reaction may take place to a short extent, failing to accomplish the desired adhesion promotion. If Mw exceeds 6,500, or if the content of components having a Mw of at least 600 exceeds 90% by weight, then adhesion promotion is not adversely affected, but the solution may become less stable due to the increased content of high-molecular-weight components; and the productivity may become low when the organic solvent and the distillation time needed in the dealcoholization crosslinking reaction are taken into account.

Another embodiment of the invention is a method for preparing the silane coupling agent defined above, comprising the steps of reacting a silane coupling agent having a succinic anhydride functional group represented by the general formula (2):

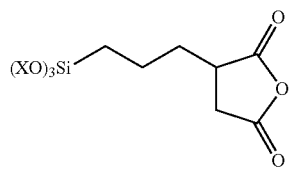

(2)

wherein X is as defined above, with a primary and/or secondary amine compound having the general formula (3):

(3)

wherein $R^1$ and $R^2$ are as defined above, in an aprotic organic solvent having a boiling point of at least 140° C., and heating the reaction solution at a temperature equal to or higher than the boiling point of the organic solvent for thereby effecting dealcoholization reaction between the carboxylic acid group and the alkoxysilyl group in the starting silane coupling agent structure while distilling off the organic solvent.

Examples of the compound having formula (2) include trimethoxysilylpropylsuccinic anhydride and To triethoxysilyipropylsuccinic anhydride. Inter alia, trimethoxysilylpropylsuccinic anhydride is preferred since it is readily available, for example, as X-12-967C from Shin-Etsu Chemical Co., Ltd.

Of the compounds having formula (3), tert-butylamine and aniline are preferred because they are readily available and the product exhibits low coloration and heat resistance.

The organic solvent used herein should desirably have a high boiling point, specifically of at least 140° C. and be aprotic. It is also desirable for the solubility of silane coupling agent reactant that the solvent be highly polar.

Suitable solvents include those commonly used in the preparation of polyimide, for example, propylene glycol monomethyl ether acetate, cyclohexanone and N-methylpyrrolidone.

First, a succinic anhydride functionality-containing silane coupling agent having formula (2) Is reacted with a primary and/or secondary amine compound having formula (3) in an aprotic organic solvent having a boiling point of at least 140° C. Although reaction conditions are not particularly limited, the reaction is preferably conducted at a temperature of 50 to 200° C., especially 60 to 140° C. for a time of 30 minutes to 24 hours, especially 1 to 10 hours.

Subsequently, the reaction solution is heated at a temperature equal to or higher than the boiling point of the organic solvent, specifically 140 to 190° C. for thereby effecting dealcoholization reaction between the carboxylic acid group and the alkoxysilyl group in the silane coupling agent structure while distilling off the organic solvent. The temperature necessary for dealcoholization reaction is preferably in the range of 140 to 190° C., but not limited thereto. At a temperature below 140° C., however, the reaction may take place at a low efficiency and fail to reach the desired degree of crosslinking. The dealcoholization reaction is preferably conducted for 1 to 24 hours, more preferably 2 to 20 hours.

The silane coupling agent of the invention finds application as a primer and adhesion promoter for resin compositions, for example. In this context, contemplated herein are a primer composition comprising the silane coupling agent and a coating composition comprising the silane coupling agent, especially a coating composition for use with photosensitive, heat-resistant materials.

When the silane coupling agent is used as a primer, the primer composition may comprise other components such as a leveling agent, thixotropic agent and diluent solvent. The other components may be any of commercially available customary products. When compounded in the primer composition, the silane coupling agent may be used in a sufficient concentration to achieve the desired adhesion promotion, specifically 0.1 to 50% by weight, more preferably 1 to 40% by weight of the composition. Less than 0.1 wt% of the silane coupling agent may fail to exert a satisfactory adhesion promotion effect. If the concentration exceeds the upper limit, the primer layer may become thicker, the adhesion promotion effect may be saturated, or adhesion may be rather degraded due to breakage of thick film portions.

One typical embodiment of the silane coupling agent serving as an adhesion promoter is to improve the adhesion of photosensitive resin compositions (coating compositions for use with photosensitive, heat-resistant materials, as described in the Background Art section) to metals (e.g., silicon, aluminum, nickel, molybdenum, chromium, palladium, cobalt, zirconium, and copper). As the photosensitive resin composition, any of well-known photoresist material compositions is applicable. Specific examples include resin compositions based on polyimide resin precursors (such as polyamic acids, polyamic acid esters, polyamic acid amides), polybenzoxazole resin precursors (such as hydroxypolyamides), heat resistant polyamide resins, and cresol-novolac based phenolic resins. Of these, the silane coupling agent is most preferably used as an adhesion promoting component for resin compositions based on polyimide resin precursors or polybenzoxazole resin precursors.

In these resin compositions, the silane coupling agent is preferably used in an amount of 0.1 to 30 parts, more preferably 1 to 20 parts by weight per 100 parts by weight of the heat-resistant resin precursor. Less than 0.1 part of the silane coupling agent may fail to exert a satisfactory is adhesion promotion effect whereas more than 30 parts may detract from the stability of varnish.

EXAMPLE

Examples and Comparative Examples are given below for illustrating the invention, but the invention is not limited thereto. In Examples, all parts are by weight, viscosity is a kinematic viscosity measured by an Ostwald viscometer. Mw is measured versus polystyrene standards by GPC using tetrahydrofuran as developing solvent, and the values of n, p, and q indicative of the composition of a reaction product are theoretical values computed from Mw.
[Preparation of Silane Coupling Agent]

Example 1

A 500-ml separable flask equipped with a stirrer, reflux condenser, and thermometer was charged with 450.0 parts of propylene glycol monomethyl ether acetate, 38.3 parts of (trimethoxysilyl)propylsuccinic anhydride (X-12-967C by Shin-Etsu Chemical Co., Ltd.), and 11.7 parts of tert-butylamine, which were heated and stirred. The contents were heated and stirred at an internal temperature of 70° C. for 1 hour. Thereafter the heating medium temperature was raised to 170° C., at which the solvent (b.p. ~146° C.) and the methanol formed by crosslinking reaction were distilled off under atmospheric pressure. The reaction was completed at the point of time when fractions were distilled off until. the theoretical solids content reached 30% by weight. The reaction product was a pale yellow clear liquid having a nonvolatile content of 27.6% by weight upon heating at 105° C. for 3 hours and a viscosity of 6.4 $mm^2/s$ at 25° C. FIG. 1 is a GPC chart of the reaction product (i.e., silane coupling agent). The silane coupling agent had a Mw of 890, contained 58% by weight based on the entire polymer of components having a Mw of at least 600, and corresponded to formula (1) wherein n=4, p=2.3, and q=1.4 as average values.

Example 2

The procedure of Example 1 was repeated except that (triethoxysilyl)propylsuccinic anhydride was used instead of (trimethoxysilyl)propylsuccinic anhydride. The reaction product was a pale yellow clear liquid having a nonvolatile content of 24.7% by weight upon heating at 105° C. for 3 hours and a viscosity of 4.6 $mm^2/s$ at 25° C. The reaction product (i.e., silane coupling agent) had a Mw of 940, contained 61% by weight based on the entire polymer of components having a Mw of at least 600, and corresponded to formula (1) wherein n=2, p=2.6, and q=1.6 as average values.

Comparative Example 1

A 500-ml separable flask equipped with a stirrer, reflux condenser, and thermometer was charged with 116.0 parts of propylene glycol monomethyl ether acetate, 38.3 parts of (trimethoxysilyl)propylsuccinic anhydride (X-12-967C by Shin-Etsu Chemical Co., Ltd.), and 11.7 parts of tert-butylamine, which were heated, stirred and mixed at an internal temperature of 40° C. for 1 hour. The reaction product was a pale yellow clear liquid having a nonvolatile content of 29.7% by weight upon heating at 105° C. for 3 hours and a viscosity of 5.0 $mm^2/s$ at 25° C. The reaction product (i.e., silane coupling agent) had a Mw of 420, contained 5% by weight based on the entire polymer of components having a Mw of at least 600, and corresponded to formula (1) wherein n=0, p=3, and q=0.
[Synthesis of Heat-resistant Resin Precursor]
  (Follow-up Test of Reference Example 1 of JP 4817710)

Synthesis Example 1

A 5-L separable flask equipped with a stirrer, reflux condenser, dropping funnel and thermometer was charged with 432.6 parts of 2,2-bis(3-amino-4-hydroxyphenyl)-hexafluoropropane, 59.3 parts of pyridine, and 1,510 parts of N,N-dimethylacetamide, which were stirred and mixed at room temperature (25° C.) into a solution. From the dropping funnel, a solution of 18.9 parts of 4-methylcyclohexane-1,2-dicarboxylic anhydride in 95 parts of γ-butyrolactone was added dropwise to the flask. After the completion of dropwise addition, the reaction mixture was stirred at room temperature (25° C.) for 2 hours and then cooled to −10° C. in a dry ice bath. From the dropping funnel, a solution of 299 parts of 4,4'-diphenyl ether dicarboxylic dichloride and 22.8 parts of isophthalic dichloride in 1,600 parts of γ-butyrolactone was added dropwise to the flask.

After the completion of dropwise addition, the cooling bath was removed, and the reaction mixture was stirred for 15 hours. Then 119 parts of pyridine was added. The reaction solution was poured into water whereupon the polymer product dispersed and precipitated. The polymer product was recovered, washed and dried, obtaining the desired hydroxypolyamide material as heat-resistant resin precursor. The polymer material had a Mw of 28,000 as measured by GPC.

[Preparation of Varnish Samples and Evaluation of Adhesion]

Examples 3, 4 and Comparative Examples 2, 3

A varnish sample was prepared by dissolving 5 parts as solids of the silane coupling agent obtained in any of Examples 1, 2 and Comparative Example 1 and 100 parts of the polymer obtained in Synthesis Example 1 in the combination shown in Table 1 in γ-butyrolactone, and passing through a filter with a trapping pore size of 0.2 μm.

The varnish sample was spin coated onto a silicon wafer, dried at 120° C. for 3 minutes, and heat treated in an inert oven of nitrogen atmosphere at 250° C. for 1 hour, to form a heat-resistant resin film. The film was subjected to a crosshatch adhesion test according to JIS K4500 before and after the pressure cooker test (PCT) of heating at 130° C. and 3 atmospheres for 100 hours. The results are shown in Table 1.

TABLE 1

| | Silane coupling agent | Crosshatch adhesion test | |
|---|---|---|---|
| | | Before PCT | After PCT |
| Example 3 | Example 1 | 100 | 100 |
| Example 4 | Example 2 | 100 | 100 |
| Comparative Example 2 | Comparative Example 1 | 100 | 40 |
| Comparative Example 3 | none | 0 | 0 |

It is evident that the heat-resistant resin film obtained by curing a varnish containing the silane coupling agent of the invention maintains good adhesion even after the PCT.

The results of Examples and Comparative Examples prove that the silane coupling agent of the invention is a satisfactory adhesion promoter for polyimide base materials.

Japanese Patent Application No. 2014-011405 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A silane coupling agent consisting of a mixture of organosilicon compounds having the general formula (1):

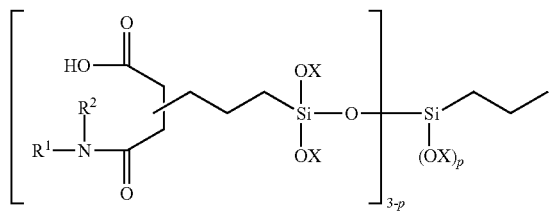

(1)

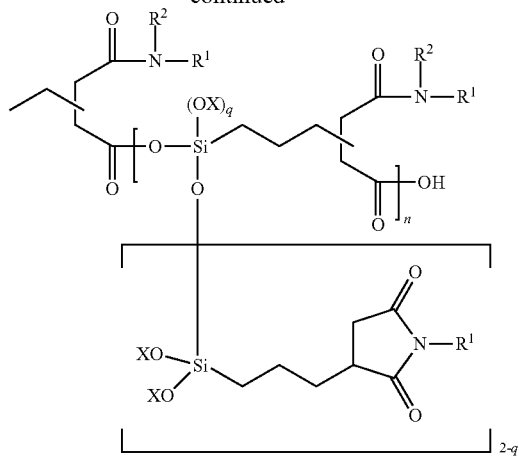

-continued wherein $R^1$ is independently $C_1$-$C_{10}$ alkyl or $C_6$-$C_{10}$ aryl, $R^2$ is independently hydrogen, $C_1$-$C_{10}$ alkyl or $C_6$-$C_{10}$ aryl, X is independently $C_1$-$C_{10}$ alkyl or $C_6$-$C_{10}$ aryl, n is an integer of at least 1, p is an integer of 0 to 3, and q is an integer of 0 to 2.

2. The silane coupling agent of claim 1 wherein $R^2$ is hydrogen.

3. The silane coupling agent of claim 2 wherein $R^1$ is tert-butyl or phenyl.

4. The silane coupling agent of claim 1, having a weight average molecular weight of at least 850 as measured versus polystyrene standards by gel permeation chromatography and containing at least 50% by weight of organosilicon compounds having a weight average molecular weight of at least 600.

5. A method for preparing the silane coupling agent of claim 1, comprising the steps of:

reacting a silane coupling agent having a succinic anhydride functional group represented by the general formula (2):

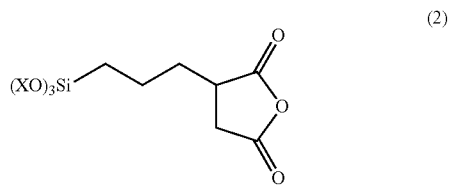

(2)

wherein X is as defined above, with a primary and/or secondary amine compound having the general formula (3):

(3)

wherein $R^1$ and $R^2$ are as defined above, in an aprotic organic solvent having a boiling point of at least 140° C., and heating the reaction solution at a temperature equal to or higher than the boiling point of the organic solvent for thereby effecting dealcoholization reaction between the carboxylic acid group and the alkoxysilyl group in the starting silane coupling agent structure while distilling off the organic solvent.

6. The method of claim 5 wherein the aprotic organic solvent is propylene glycol monomethyl ether acetate, cyclohexanone or N-methylpyrrolidone.

7. A primer composition comprising:
a silane coupling agent consisting of a mixture of organosilicon compounds having the general formula(1):

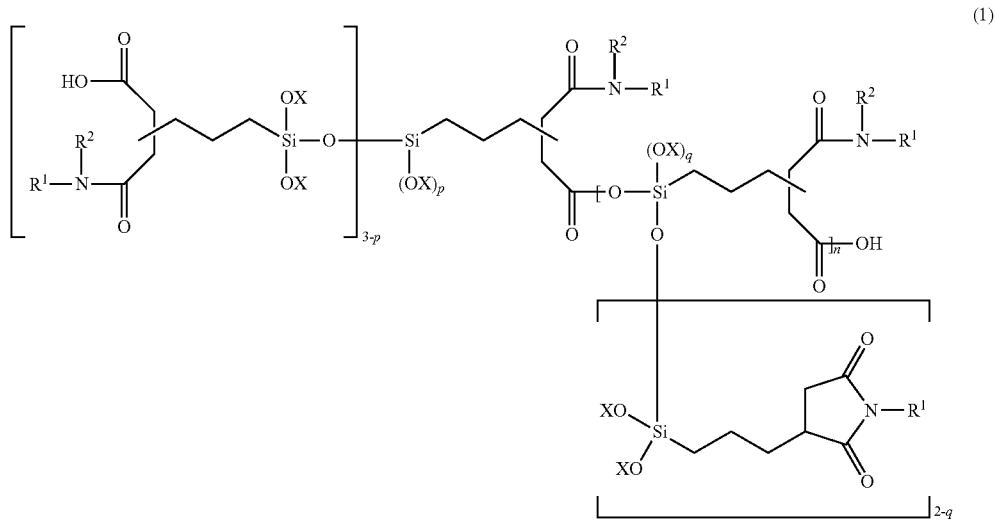

wherein $R^1$ is independently $C_1$-$C_{10}$ alkyl or $C_6$-$C_{10}$ aryl, $R^2$ is independently hydrogen, $C_1$-$C_{10}$ alkyl or $C_6$-$C_{10}$ aryl, X is independently $C_1$-$C_{10}$ alkyl or $C_6$-$C_{10}$ aryl, n is an integer of at least 1, p is an integer of 0 to 3, and q is an integer of 0 to 2; and
an additional primer component.

8. A coating composition comprising:
a silane coupling agent consisting of a mixture of organosilicon compounds having the general formula (1):

wherein $R^1$ is independently $C_1$-$C_{10}$ alkyl or $C_6$-$C_{10}$ aryl, $R^2$ is independently hydrogen, $C_1$-$C_{10}$ alkyl or $C_6$-$C_{10}$ aryl, X is independently $C_1$-$C_{10}$ alkyl or $C_6$-$C_{10}$ aryl, n is an integer of at least 1, p is an integer of 0 to 3, and q is an integer of 0 to 2; and
an additional coating component.

9. The coating composition of claim 8, suited for use with a photosensitive heat-resistant material.

10. An article having a cured film prepared by curing a coating composition comprising:

a silane coupling agent consisting of a mixture of organosilicon compounds having the general formula(1):

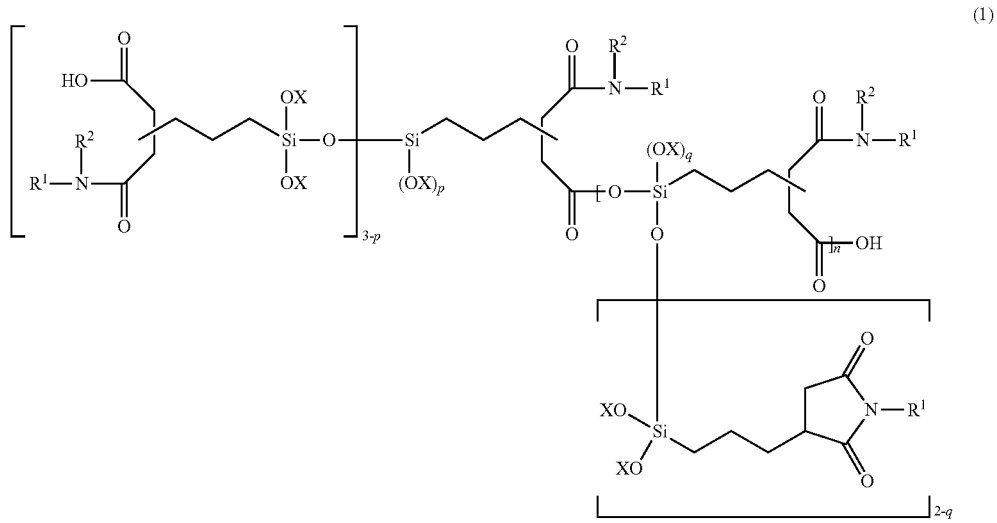

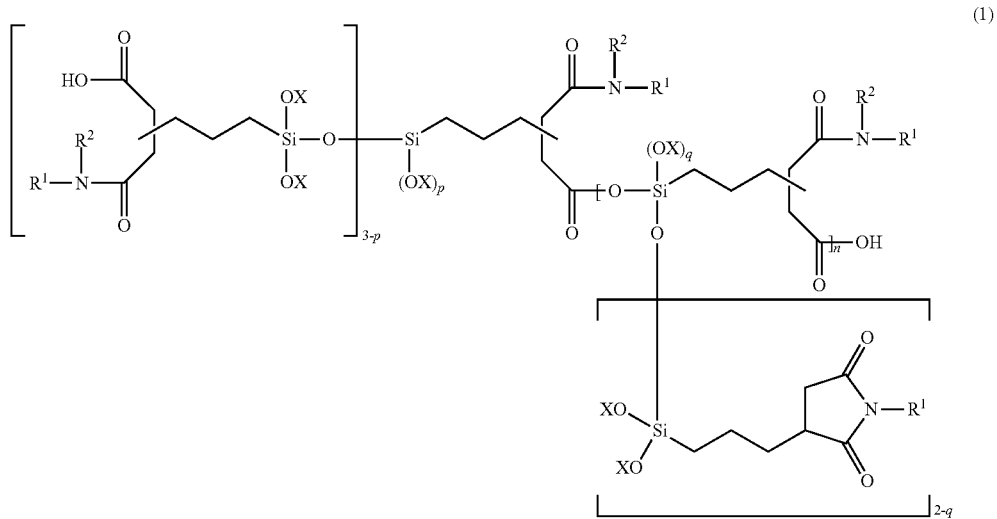

(1)

wherein R¹ is independently $C_1$-$C_{10}$ alkyl or $C_6$-$C_{10}$ aryl, R² is independently hydrogen, $C_1$-$C_{10}$ alkyl or $C_6$-$C_{10}$ aryl, X is independently $C_1$-$C_{10}$ alkyl or $C_6$-$C_{10}$ aryl, n is an integer of at least 1, p is an integer of 0 to 3, and q is an integer of 0 to 2.

11. A varnish comprising:

a silane coupling agent consisting of a mixture of organosilicon compounds having the general formula(1):

wherein R¹ is independently $C_1$-$C_{10}$ alkyl or $C_6$-$C_{10}$ aryl, R² is independently hydrogen, $C_1$-$C_{10}$ alkyl or $C_6$-$C_{10}$ aryl, X is independently $C_1$-$C_{10}$ alkyl or $C_6$-$C_{10}$ aryl, n is an integer of at least 1, p is an integer of 0 to 3, and q is an integer of 0 to 2; and a polymer.

12. A resin film comprising:

a silane coupling agent consisting of a mixture of organosilicon compounds having the general formula(1):

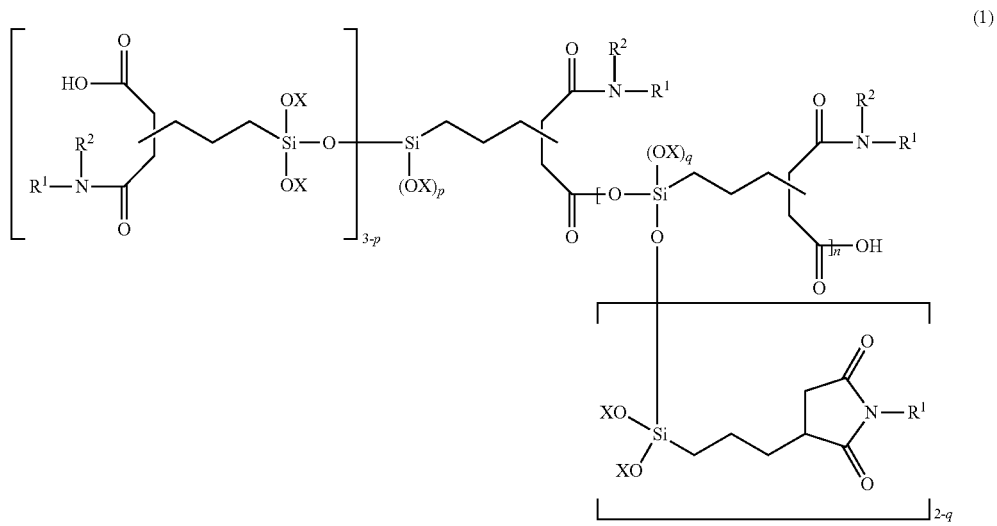

(1)

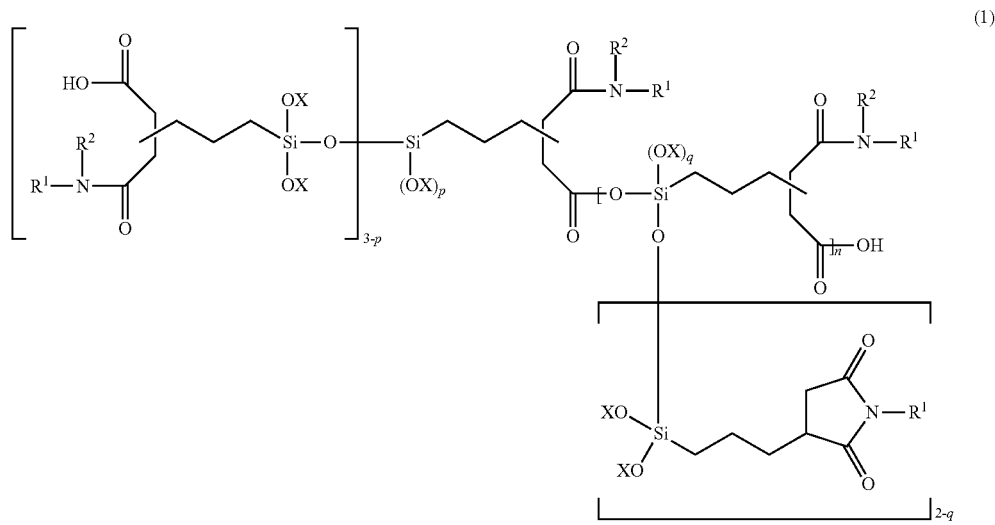

wherein $R^1$ is independently $C_1$-$C_{10}$ alkyl or $C_6$-$C_{10}$ aryl, $R^2$ is independently hydrogen, $C_1$-$C_{10}$ alkyl or $C_6$-$C_{10}$ aryl, X is independently $C_1$-$C_{10}$ alkyl or $C_6$-$C_{10}$ aryl, n is an integer of at least 1, p is an integer of 0 to 3, and q is an integer of 0 to 2; and a polymer.

13. The primer composition of claim 7, wherein the silane coupling agent is 0.1 to 50% by weight.

14. The coating composition of claim 8, wherein the silane coupling agent is 0.1 to 30 parts by weight per 100 parts by weight of the polymer.

15. The resin film of claim 12, wherein the film is in contact with metal.

16. The resin film of claim 12, wherein the film is in contact with silicon.

* * * * *